United States Patent [19]

Ryabinin et al.

[11] Patent Number: 5,606,098

[45] Date of Patent: Feb. 25, 1997

[54] AMIDES AND ESTERS OF PERFLUOROPOLYOXAALKYLENE-SULFO- OR PERFLUOROPOLYOXAALKYLENE-CARBOXYLIC ACIDS AND A PROCESS FOR PRODUCING SAME

[75] Inventors: Nikolai A. Ryabinin; Aleksandr N. Ryabinin, both of Sankt-Peterburg, Russian Federation

[73] Assignee: AO "Avtokoninvest", Moscow, Russian Federation

[21] Appl. No.: 530,233

[22] PCT Filed: Jan. 30, 1995

[86] PCT No.: PCT/RU95/00014

§ 371 Date: Oct. 3, 1995

§ 102(e) Date: Oct. 3, 1995

[87] PCT Pub. No.: WO95/21209

PCT Pub. Date: Aug. 10, 1995

[30] Foreign Application Priority Data

Feb. 4, 1994 [RU] Russian Federation ............. 94004093

[51] Int. Cl.$^6$ ........................ C07C 69/66; C07C 231/00
[52] U.S. Cl. ........................... 560/184; 564/96; 564/144
[58] Field of Search ........................... 560/184; 564/96, 564/144

[56] References Cited

U.S. PATENT DOCUMENTS

| 3,553,179 | 1/1971 | Bartlett et al. ........................ 260/80.72 |
| 3,845,051 | 10/1974 | Zollinger et al. ........................ 280/248 |

FOREIGN PATENT DOCUMENTS

| 338530 | 4/1989 | European Pat. Off. . |
| 338529 | 4/1989 | European Pat. Off. . |
| 519406 | 6/1992 | European Pat. Off. . |
| 445356 | 9/1971 | U.S.S.R. . |
| 1252364 | 11/1984 | U.S.S.R. . |
| 1419009 | 9/1986 | U.S.S.R. . |
| 1761817 | 11/1989 | U.S.S.R. . |
| 1074768 | 8/1965 | United Kingdom . |
| 2053252 | 6/1980 | United Kingdom . |

OTHER PUBLICATIONS

"Recent Advancement in Technology of Fluorine Compounds," by N. Ishikawa, Mir Publishers, Moscow, p. 399.
*Chemistry and Technology of Fuels and Oils*, No. 10, p. 30, 1992.
*Chemistry and Technology of Fuels and Oils*, No. 4, pp. 36–38, 1992.

*Primary Examiner*—Gary Geist
*Assistant Examiner*—Rosalynd A. Williams
*Attorney, Agent, or Firm*—Lowe, Price, LeBlanc & Becker

[57] ABSTRACT

Amides and esters of perfluoropolyoxaalkylene-sulfo- or perfluoropolyoxaalkylene-carboxylic acids of the general following formula:

$R_F R_F' Z Q$, where $R_F = CF_3O-$, $C_2F_5O-$, $C_3F_7O-$, $C_8F_{17}O-$, $R_F' =$ $$-(\underset{\underset{CF_3}{|}}{C}FCF_2O)_n\underset{\underset{CF_3}{|}}{C}F-,$$

$-(CF_2CF_2O-)_nCF_2-$, $-(CF_2CF_2CF_2O)_nCF_2CF_2-$, where n=8–55;

$Z = -CO-$, $-SO_2-$, $Q = -N(C_mH_{2m}OH)_2$, where m=2, 3, 4, 6, 8, 10

$-N[(C_2H_4O)_4C_3H_6OH]_2$, $-NH-C_2H_4OR\eta$, where $R\eta = CH_3-$, $C_2H_5-$, $C_3H_7-$, $-NH(C_2H_4O)_5H$, $-OC_lH_{2l}N(C_lH_{2l}OH)_2$, where $\eta=1, 2, 4$ $C_kH_{2k+1}O-$, where k=6, 8, 10.

4 Claims, No Drawings

AMIDES AND ESTERS OF PERFLUOROPOLYOXAALKYLENE-SULFO- OR PERFLUOROPOLYOXAALKYLENE-CARBOXYLIC ACIDS AND A PROCESS FOR PRODUCING SAME

TECHNICAL FIELD

This application is a 371 of PCT/RV95/00014, filed Jan. 30, 1995.

The present invention relates to novel compounds, that is, amides and esters of perfluoropolyoxaalkylene-sulfo- or perfluoropolyoxaalkylene-carboxylic acids and to a process for producing same.

The aforementioned compounds can be used for producing antifriction-, antiscuff-, and antiwear additives to lubricating oils and greases: additionally, they are applicable as protective coatings against atmospheric corrosion.

BACKGROUND ART

Known in art presently are compounds based on thermally destructed polytetrafluoroethylene and used as an additive to motor lubricating oils (GB, 1,074,768), the application of which makes it possible to enhance the wear-resistance of the friction units of an engine by 30 to 50%. However, such an additive features but low durability and adhesion strength when applied to solid surfaces, this being due to sedimentation. Furthermore, it cannot be used in systems with a centrifugal cleaning or filtering of oil (e.g., diesel ones), because the polytetrafluoroethylene particles are retained by the filtering elements of oil-cleaning systems.

One more additive to lubricating oil is known to be based on phosphate-(à,à-dihydroperfluoroalkyl) alcohol (Isikawa, N., "Recent advancement in technology of fluorine compounds", Moscow, Mir Publishers, p.399 (a translation into the Russian from an English edition). However, such an additive features but a low level of antiwear and antiscuff properties and low stability in the zone of friction. Additionally, it causes metal corrosion.

Known in the present state of the art is also use of perfluoropolyoxapropylene-carboxylic acid as the base of antiscuff and antiwear additives to consistent (plastic) greases (cf. the journal "Chemistry and technology of fuels and oils", 1992, No.10, p.30 (in Russian), as well as a component of compositions for treating metal-cutting tools and friction units with a view to extending their service durability (SU, A, 445,356; 1,252,364; 1,419,009; 1,761, 817), and also as the base of lubricating oils and greases (cf. the journal "Chemistry and technology of fuels and oils", 1992, No.4, pp.36–38 (in Russian).

However, the aforementioned compounds are neither dissolved nor emulsified in lubricating oils so that to obtain emulsions of said compounds involves use of a scarcely available and costly fluorine-containing emulsifier.

In addition, a process for producing said compounds is much sophisticated and time-consuming.

DISCLOSURE OF THE INVENTION

The present invention has for its principal object to provide novel compounds that are readily emulsifiable in lubricating oils, feature high heat stability, as well as high adhesion-, antiwear-, antiscuff-, and corrosion-resisting properties and are therefore applicable in friction units of various machinery and mechanisms, such as diesel-, carburetor-, and some other engines, gear reducers, power transmissions, etc.

The foregoing object is accomplished due to proposal of such novel compounds as perfluoropolyoxaalkylene-sulfo- or perfluoropolyoxaalkylene-carboxylic acids which, according to invention, have the following general formula: $R_F R_F' ZQ$, where $R_F = CF_3O-$, $C_2F_5O-$, $C_3F_7O-$, $C_8F_{17}O-$, $R_F' =$

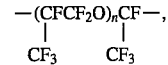

$-(CF_2CF_2O-)_n CF_2-$,
$-(CF_2CF_2CF_2O)_n CF_2CF_2-$,
where $n = 8-55$;
$Z = -CO-$, $-SO_2-$,
$Q = -N(C_m H_{2m} OH)_2$, where $m = 2, 3, 4, 6, 8, 10$
$-N[(C_2H_4O)_4 C_3H_6OH]_2$,
$-NH-C_2H_4 OR_\eta$, where $R_\eta = CH_3-$, $C_2H_5-$, $C_3H_7-$,
$-NH(C_2H_4O)_5 H$,
$-OC_1H_{21}N(C_1H_{21}OH)_2$, where $\eta = 1, 2, 4$
$C_k H_{2k+1} O-$, where $k = 6, 8, 10$.

Neither said compounds nor a process for their production has heretofore been described in literature.

The compounds proposed herein are in fact colorless or faintly yellow liquids having a viscosity of 600–3500 cSt, a density of 1620–1810 kg/m³, and a congelation point of plus 36° to minus 65° C.

The structure of said compounds is confirmed by the data of IR- and NMR-spectroscopy of $^{19}F$ and by those of an elementary analysis.

The herein-proposed compounds contain diverse functional groups which enable said compounds to be in widespread use as a base of antifriction- and antiscuff additives for various lubricating oils and hydraulic fluids having a broad range of action (antiwear and corrosion-resisting) in a wide temperature range (from −35° to +450° C.) and a prolonged service period. The proposed compounds are adsorbable on solid surfaces, thus reducing their surface energy from 1800–6000 æN/m to 4–6 æN/m, the friction coefficient by 10–20 times, and the moment of static friction by $10^2$–$10^4$ times and increasing the tangential shearing force of an oil or a hydrocarbon fluid on a solid surface by 70–75 times; in addition, said compounds feature high vapor pressure equal to $10^{-13}$–$10^{-14}$ torr, are thermally stable to a temperature of 450° C., incombustible, explosion- and fireproof, and nontoxic (4th class of danger).

An important merit of the proposed compounds is their availability and a possibility of obtaining their derivatives featuring different solubility and emulsifying power with respect to lubricating oils.

Additionally, no deficient raw materials are required for producing the proposed compounds.

Another object of the present invention is to provide a simple process for producing said novel compounds.

According to the invention, the process for producing amides and esters of perfluoropolyoxaalkylene-sulfo- or perfluoropolyoxaalkylene-carboxylic acids consists in that fluoroanhydride of perfluoropolyoxaalkylene-sulfo- or perfluoropolyoxaalkylene-carboxylic acid having the following general formula:
$R_F R_F' ZQ$, where
$R_F = CF_3O-$, $C_2F_5O-$, $C_3F_7O-$, $C_8F_{17}O-$, $R_F' =$

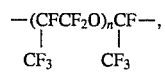

$(CF_2CF_2O-)_nCF_2-$, $(CF_2CF_2CF_2O)_nCF_2CF_2-$,
where n=8–55;
$Z=-CO-, -SO_2-$,
is mixed with a primary, secondary, or tertiary amine or alkanolamines of a general formula:
$H_{3-x}N(R)_x$, where x=1, 2, 3
  $R=(C_nH_{2n}OH)_x$, where n=2, 3, 4, 6, 8, 10
  $-[(C_2H_4O)_4C_3H_6OH]_x$, with x=2,
  $-(C_2H_4OCH_3)_x$,
  $-(C_2H_4OC_2H_5)_x$,
  $-(C_2H_4OC_3H_7)_x$, with x=1,
  $-[(C_2H_4O)_5H]_x$, and
  $-(C_nH_{2n}OH)_x$, where n=2, 4 with x=3,
or with higher fatty alcohols of a general formula:
$C_nH_{2n+1}OH$, where n=6, 8, 10,
and a compound selected from the group consisting of a fluoride of an alkali- and an alkaline-earth metal, ammonium fluoride, or aluminium fluoride, as well as carbonates and bicarbonates of metals, with a molar ratio between said components of 1.0:1.2 to 4.0:1.5–3.0, respectively, followed by heating the reaction mixture to 40°–60° C., holding said mixture at that temperature, and isolating the end product from the resultant reaction mass.

As has been stated hereinbefore, the reactants are mixed together at a reduced temperature of the order of from –25° to +8° C. It is under such conditions that the end product features a good yield and the production process proceeds within an optimum period of time. Further heating of the mixture resultant from intermixing of the above components, to 40°–60° C. and holding said mixture at that temperature provide for a more complete running of the reaction (that is, with an adequately high degree of conversion), which also tells positively on the yield of the end product.

The ratio between the reactants is so selected as to provide in every case a maximum yield and a highest degree of purity of the end product, as well as a minimum duration of the production process.

When using fluoroanhydrides of perfluoropolyoxaalkylene- sulfo- or perfluoropolyoxaalkylene-carboxylic acids having a molecular weight above 2000, it is expedient that the aforementioned components are mixed together in the presence of polyfluorocarbons used as a solvent and that the resultant mixture is boiled at a boiling point of the solvent selected. It is recommended that used as polyfluorocarbon solvents are, e.g., trifluorotrichloroethane (Freon-113), or perfluorotriethylamine.

Use of polyfluorocarbon solvents makes it possible to carry out amidation and esterification reactions in a homogeneous phase, whereas a fluorine-containing component and the products of its reaction are insoluble in hydrocarbon solvents.

The proposed process for producing amides and esters of perfluoropolyoxaalkylene-sulfo- or perfluoropolyoxaalkylene-carboxylic acids is technologically simple and is carried out as follows.

The following reactants are mixed together in a reaction vessel equipped with a stirrer, a thermometer, a refluxer, and a jacket: fluoroanhydride of perfluoropolyoxaalkylene-sulfo- or perfluoropolyoxaalkylene-carboxylic acid (perfluoropolyoxaalkylene-sulfofluoride), a primary, a secondary, or a tertiary amine or alkanolamine, or else a higher fatty alcohol, as well as a fluoride of an alkali- and an alkaline-earth metal, or ammonium fluoride, or aluminium fluoride, or a metal carbonate, or a metal bicarbonate, with a preselected molar ratio between said components, in the medium of a fluorine-containing solvent, or without the latter, at a reduced temperature of the order of from –25° to +8° C. Then the resultant mixture is boiled or heated to 40°–60° C. over a water bath with refluxer under constant stirring for 40–240 min, whereupon the end product is isolated from the resultant reaction mass, using routine techniques. Next the organic layer is separated, purified in a cationic column, then in an anionic column, dried with $MgSO_4$ or $Na_2SO_4$, after which the solvent is removed (if any), and the residue is extracted with ethyl, n-propyl, or isopropyl alcohol, and passed through a filter. Finally, the alcohol is distilled off from the purified filtrate, and the still bottoms are vacuum-dried.

EMBODIMENTS OF THE INVENTION

Example 1

30 g (0.024 mole) of fluoroanhydride of perfluoropolyoxapropylene-carboxylic acid

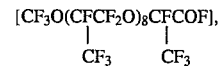

2.52 g (0.024 mole) of diethanolamine, and 1.1 g (0,03 mole) $NH_4F$ are mixed together at +5° C.

The resultant mixture is heated to 60° C. with a refluxer under constant stirring and held at that temperature for 40 min, whereupon the reaction mass is washed three times in succession with 50 ml of distilled water. Once water has been separated, the reaction mass is purified first in a cationic column, then in an anionic column, dried with fused $Na_2SO_4$, and passed through a filter.

The stillage residue is extracted three times in succession with 50 ml of an absolute isopropyl alcohol, the extract is filtered, and the alcohol is distilled off from the filtrate. The stillage residue, i.e., diethanolamide of perfluoropolyoxapropylene-carboxylic acid is vacuum-dried at 1 mm Hg and 65° C. for two hours. The yield of the end product is 29.4 g (93%), the congelation point, –65° C., $F'=0.002$ wt. %.

IR-spectrum ($CaF_2$), v, $cm^{-1}$:

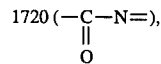

3350 (—OH)
NMR-spectrum of $^{19}F$ in $CCl_3F$, δ, p.p.m.: 55.8 $CF_3O-$, 82.0 $-OCF_2-$, 143 $-OCF$, 81.4 $-CF_3$, 130.8 $-\underset{|}{C}FCON=$.

Found, %: C, 23.2; H, 0.58; F, 63.2; N, 0.86.
$C_{32}H_{10}F_{55}O_{12}N$.
Calculated, %: C, 23.3; H, 0.60; F, 63.5; N, 0.85.
The molecular weight of the product equals 1640.

Example 2

25 g (0.018 mole) of perfluoropolyoxaethylenesulfo-fluoride $[C_2F_5O(CF_2CF_2O)_{10}(CF_2)_2SO_2F]$, 7.56 g (0.072 mole) of diethanolamine, and 1.45 g (0.025 mole) KF are mixed together at +2° C.

Then the resultant mixture is heated to 40° C. with a refluxer under constant stirring and held at that temperature for three hours, whereupon the reaction mass is washed three times in succession with 50 ml of distilled water and purified first in a cationite column, then in an anionite column.

Next the reaction mass is dried with fused $Na_2SO_4$ and passed through a filter. The stillage residue is extracted three times in succession with 30 ml of an absolute ethyl alcohol and the extract is filtered. The alcohol is distilled off from the filtrate and the stillage residue, i.e., diethanolamide of perfluoropolyoxaethylene-sulfo acid is vacuum-dried at 1 mm Hg and 50° C. for two hours. The yield of the end product is 18.6 g (72%), the congelation points −44° C., $F'$=0.009 wt. %.

IR-spectrum ($CaF_2$), ν, $cm^{-1}$: 1420 ($CF_2$—$SO_2$—N=), 3350 (—OH).

NMR-spectrum of $^{19}F$ in $CCl_3F$, δ, p.p.m.: 55.5 $CF_3O$—, 91.0 —$OCF_2$—, 86.0 $CF_2$—$CF_2$—S,

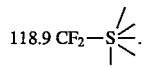

Found, %: C, 21.8; H, 0.70; F, 59.9; N, 0.90; S, 2.1.
$C_{28}H_{10}F_{49}O_{15}NS$.
Calculated, %: C, 21.5; H, 0.64; N, 0.90; F, 59.5; S, 2.0.
Molecular weight of the product is 1560.

Example 3

32 g (0.014 mole) of fluoroanhydride of perfluoropolyoxapropylene-carboxylic acid

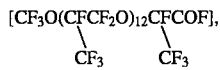

13.2 g (0.025 mole) of didecanolamine, 2.0 g (0.02 mole) $KHCO_3$, and 50 g of Freon-113 are mixed together at 0° C. The mixture is boiled with a refluxer under stirring for 40 min, whereupon the reaction mass is washed three times in succession with 40 ml of distilled water and purified first in a cationic column, then in an anionic column. The organic layer is dried with $MgSO_4$ and filtered, Freon-13 is distilled off. The organic residue is extracted three times in succession with 50 ml of an absolute isopropyl alcohol and the extract is passed through a filter to get rid of substances insoluble in isopropyl alcohol. The alcohol is distilled off, and the residue, i.e., didecanolamide of perfluoropolyoxapropylene-carboxylic acid is vacuum-dried at 1 mm Hg and 50° C. for 2.5 hours. The yield is 19.9 g (50%), the congelation point, −25° C., $F'$=0.001 wt. %.

IR-spectrum ($CaF_2$), ν, $cm^{-1}$:

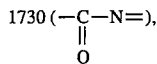

3330 (—OH).

NMR-spectrum of $^{19}F$ in $CCl_3F$, δ, p.p.m.: 81.7 $CF_3$—, 130.0 —$CF_2$—, 82.2 —$CF_2O$—, 141.0 OCF, 131.1 —OCF—CON=.

Found, %: C, 28.4; H, 1.6; N, 0.5; N, 0.90; F, 60.0.
$C_{62}H_{24}F_{83}O_{16}N$.
Calculated, %: C, 28.3; H, 1.6; N, 0.5; F, 59.8.
Molecular weight of the product is 2610.

Example 4

45 g (0.0076 mole) of perfluoropolyoxaethylenesulfofluoride [$CF_3O(CF_2CF_2O)_{49}$ $CF_2CF_2$ $SO_2F$], 2.1 g (0.02 mole) of diethanolamine, 0.45 g (0.009 mole) KF, and 60 g of perfluorotriethylamine are mixed together at +5° C. The mixture is boiled with a refluxer under stirring for 60 min, whereupon the reaction mass is washed three times in succession with 60 ml of distilled water. The organic layer is separated and purified first in a cationic column, then in an anionic column, then dried with $MgSO_4$ and filtered, whereupon perfluorotriethylamine is distilled off. The stillage residue is extracted three times with 70 ml of an absolute isopropyl alcohol, the extract is filtered off from insoluble admixtures. The alcohol is distilled off and the residue, that is, diethanolamide of perfluoropolyoxaethylene-carboxylic acid is vacuum-dried at 1 mm Hg and 50° C. for two hours. The yield is 18.25 g (40%), the congelation point, −35° C., $F'$=0.002 wt. %.

IR-spectrum ($CaF_2$), ν, $cm^{-1}$: 1420 (—$SO_2$—N=), 3310 (—OH).

NMR-spectrum of $^{19}F$ in $CCl_3F$, δ, p.p.m.: 56.0 $CF_3O$—, 91.0 —$OCF_2$—, 80.0 —$OCF_2$—$CF_2$—, 121.4 —$CF_2$—$SO_2$—.

Found, %: C, 21.0; H, 0.17; N, 0.2; F, 63.3; S, 0.48.
$C_{105}F_{203}H_{10}O_{54}NS$.
Calculated, %: C, 20.9; H, 0.16; N, 0.2; F, 63.7; S, 0.5.
Molecular weight of the product is 6030.

Example 5

28 g (0.012 mole) of perfluoro-n-polyoxapropylenesulfofluoride [$C_2F_5$)($CF_2CF_2CF_2O)_{12}CF_2CF_2SO_2F$], 2.52 g (0.024 mole) of diethanolamine, 2 g (0.02 mole) $KHCO_3$, and 50 g of perfluorotriethylamine are mixed together at +8° C. The mixture is boiled with a refluxer under stirring for 90 min, whereupon the reaction mass is washed three times in succession with 50 ml of distilled water. The organic layer is separated and purified first in a cationic column, then in an anionic column, then dried with $MgSO_4$ and filtered, after which perfluorotriethylamine is distilled off. The stillage residue is extracted three times with 60 ml of an absolute ethyl alcohol, the extract is filtered, and the alcohol is distilled off. The resultant diethanolamide of perfluoro-n-polyoxapropylenesulfo acid is vacuum-dried at 1 mm Hg and 60° C. for two hours. The yield is 18.2 g (62%), the congelation point, −42° C., $F'$=0.004 wt. %.

IR-spectrum ($CaF_2$), ν, $cm^{-1}$: 1410 (—$SO_2$—N=), 3330 (—OH).

NMR-spectrum of $^{19}F$ in $CCl_3F$, δ, p.p.m.: 88.5 $CF_3$, 89.5 —$CF_2O$—, 85.5 —$OCF_2$—, 130.0 —$CF_2$—, 84.0 $CF_2O$—, 81 —$OCF_2$—, 119.5 —$CF_2$—S

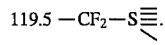

Found, %: C, 22.0; H, 0.44; N, 0.2; F, 63.8; N, 0.58; S, 1.25.
$C_{44}F_{81}O_{17}H_{10}NS$.
Calculated, %: C, 22.1; H, 0.4; F, 64.2; N, 0.6; S, 1.3.
Molecular weight of the product is 2400.

Example 6

50 g (0.014 mole) of fluoroanhydride of perfluoropoly-oxapropylene-carboxylic acid

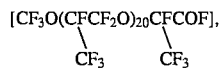
[CF$_3$O(CFCF$_2$O)$_{20}$CFCOF],
         |            |
        CF$_3$       CF$_3$ 5.4 g (0.02 mole) dioctanolamine, 1.1 g (0.03 mole) NH$_4$F, and 50 g of Freon-113 are mixed together at 0° C. and the resultant mixture is boiled with a refluxer under stirring for 90 min, whereupon the reaction mass is washed three times in succession with 50 ml of distilled water. The organic portion is dried with MgSO$_4$ and filtered, and Freon-113 is distilled off. The stillage residue is extracted three times with 50 ml of isopropyl alcohol, the extract is filtered, the alcohol is distilled off from the filtrate, and the residue, i.e., dioctanolamide of perfluoropolyoxapropylene-carboxylic acid is vacuum-dried at 1 mm Hg and 60° C. for 2.5 hours.

The yield is 14.5 g (27%), the congelation point, −38° C., F'=0.0008 wt. %.

IR-spectrum (CaF$_2$), ν, cm$^{-1}$: 1730 (—CO—N=), 3310 (—OH).

NMR-spectrum of $^{19}$F in CCl$_3$F, δ, p.p.m.: 56.0 CF$_3$O, 81.2 —CF$_3$, 81.8 —OCF$_2$,

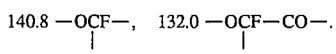
140.8 —OCF—,  132.0 —OCF—CO—.
         |              |

Found, %: C, 25.1; H, 1.0; N, 0.2; F, 63.1; N, 0.4. C$_{80}$F$_{127}$O$_{24}$H$_{34}$N.
Calculated, %: C, 25.2; H, 0.9; F, 63.4; N, 0.4.
Molecular weight of the product is 3800.

Example 7

50 g (0.01 mole) of fluoroanhydride of perfluoropolyoxapropylene-carboxylic acid

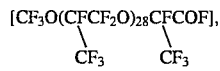
[CF$_3$O(CFCF$_2$O)$_{28}$CFCOF],
         |            |
        CF$_3$       CF$_3$ 3.22 g (0.02 mole) of dibutanolamine, 0.74 g (0.02 mole) NH$_4$F, and 50 g of Freon-1 13 are mixed together at 0° C. The resultant mixture is boiled with a refluxer under stirring for 60 min, whereupon the reaction mass is washed three times in succession with 50 ml of distilled water and purified in a cationic column and in an anionic column, then dried with MgSO$_4$ and filtered, while Freon-113 is distilled off. The stillage residue is extracted three times with 50 ml of isopropyl alcohol. The extract is filtered, the alcohol is distilled off and the residue, i.e., dibutanolamide of perfluoropolyoxapropylene-carboxylic acid is vacuum-dried at a residual pressure of 1 mm Hg and a temperature of 60° C. for two hours.

The yield is 42 g (82%), the congelation point, −48° C., F'=0.0022 wt. %.

IR-spectrum (CaF$_2$), ν, cm$^{-1}$: 1730 (—CO—N=), 3350 (—OH).

NMR-spectrum of $^{19}$F in CCl$_3$F, δ, p.p.m.: 81.5 —CF$_3$, 130.8 —CF$_2$—, 81.8 CF$_2$O,

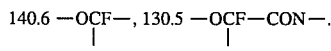
140.6 —OCF—, 130.5 —OCF—CON—.
         |             |

Found, %: C, 23.00; H, 0.37; F, 66.20; N, 0.27. C$_{98}$H$_{18}$F$_{179}$NO$_{32}$.
Calculated, %: C, 22.96; H, 0.35; F, 66.40 N, 0.27.
Molecular weight of the product is 5120.

Example 8

40 g (0.014 mole) of fluoroanhydride of perfluoropolyoxapropylene-carboxylic acid [CF$_3$O(CF$_2$CF$_2$CF$_2$O)$_{15}$CF$_2$CF$_2$COF], 1.9 g (0.028 mole) of dipropanolamine, 50 g of Freon-113 and 2.3 g (0.04 mole) of KF are mixed together at +0.

The mixture is boiled with a refluxer under stirring for 40 min, whereupon the reaction mass is washed three times in succession with 50 ml of distilled water. The organic layer is separated and purified first in a cationic column, then in an anionic column, dried with MgSO$_4$ and filtered, after which Freon-113 is distilled off. The stillage residue is extracted three times with 70 ml of isopropyl alcohol, the extract is filtered, and the alcohol is distilled off. The resultant dipropanolamide of perfluoro-n-polyoxapropylene-carboxylic acid is vacuum-dried at 1 mm Hg and 50° C. for two hours.

The yield is 29 g (70%), the congelation point, −47° C., F'=0.0008 wt. %.

IR-spectrum (CaF$_2$), ν, cm$^{-1}$:

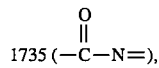
         O
         ‖
1735 (—C—N=), 3310 (—OH).

NMR-spectrum of $^{19}$F in CCl$_3$F, δ, p.p.m.: 55.8 CF$_3$O, 82.8 —OCF$_2$—, 131.0 —CF$_2$—, 84.0 —OCF$_2$—, 118.5 CF$_2$—OC—N=.

Found, %: C, 23.2; H, 0.6; F, 64.3; N, 0.49. S, 1.25. C$_{55}$H$_{14}$F$_{97}$O$_{19}$N.
Calculated, %: C, 23.3; H, 0.5; F, 65.0; N, 0.5.
Molecular weight of the product is 2830.

Example 9

50 g (0.027 mole) of fluoroanhydride of perfluorooctylhydroxypolyoxaethylene-carboxylic acid [C$_8$F$_{17}$O(CF$_2$CF$_2$O)$_{11}$CF$_2$COF] 7 g (0.032 mole) of dihexanolamine, 70 g of Freon-113, and 1.85 g (0.05 mole) NH$_4$F are mixed together at 0° C.

The mixture is boiled with a refluxer under stirring for 60 min, whereupon the reaction mass is washed three times in succession with 60 ml of distilled water and purified in a cationic column, then in an anionic column. The organic layer is separated, dried with MgSO$_4$ and filtered, after which Freon-113 distilled off. The stillage residue is extracted three times with 80 ml of n-propyl alcohol, the extract is filtered, and the alcohol is distilled off. The resultant dihexanolamide of perfluorooctylhydroxypolyoxaethylene-carboxylic acid is vacuum-dried at 1 mm Hg and 50° C. for three hours.

The yield is 33 g (60%), the congelation point, −34° C., F'=0.001 wt. %.

IR-spectrum (CaF$_2$), ν, cm$^{-1}$:

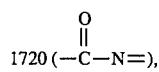
         O
         ‖
1720 (—C—N=), 3330 (—OH).

NMR-spectrum of $^{19}F$ in $CCl_3F$, δ, p.p.m.: 81.4 —$CF_3$—, 126.7 —$CF_2$—, 123.7—$CF_2$, 123.0 —$CF_2$—, 122.8 —$CF_2$—, 124.1 —$CF_2$—, 129.0 $CF_2O$—, 82.5 —$CF_2O$—, 91.0 $OCF_2$—,

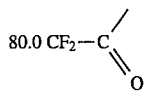

Found, %: C, 26.3; H, 1.35; F, 57.3; N, 0.7. $C_{44}F_{63}O_{15}H_{26}N$.

Calculated, %: C, 26.3; H, 1.3; F, 59.7; N, 0.7.

Molecular weight of the product is . . .

Example 10

80 g (0.008 mole) of fluoroanhydride of perfluoropolyoxapropylene-carboxylic acid

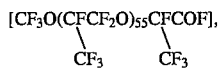

11.6 g (0.024 mole) of ditetrahydroxyethylenepropanolamine, 120 g of Freon-113, 4.2 g (0.05 mole) $NaHCO_3$ are mixed together at +1° C.

The resultant mixture is boiled with a refluxer under stirring for 90 min, whereupon the reaction mass is washed three times in succession with 100 ml of distilled water. The organic layer is separated, purified in a cationic column and in an anionic column, then dried with $MgSO_4$ and filtered, while Freon-113 is distilled off. The stillage residue is extracted three times with 80 ml of isopropyl alcohol. The extract is filtered and the alcohol is distilled off. The resultant bistetrahydroxyethylenepropanolamide of perfluoropolyoxapropylene-carboxylic acid is vacuum-dried at 1 mm Hg and 50° C. for four hours.

The yield is 40.5 g (48%), the congelation point, –28° C., $F'$=0.0009 wt. %.

IR-spectrum ($CaF_2$), ν, $cm^{-1}$:

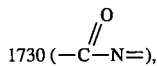

3300 (—OH).

NMR-spectrum of $^{19}F$ in $CCl_3F$, δ, p.p.m.: 55.6 $CF_3O$—, 81.5 —$CF_3$, 82.3 —$OCF_2$—, 141.3 —OCF—,

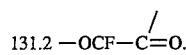

Found, %: C, 22.7; H, 0.50; F, 64.5; N, 0.13. $C_{191}F_{337}H_{46}O_{67}N$.

Calculated, %: C, 23.3; H, 0.46; F, 65.1 N, 0.14.

Molecular weight of the product is 9820.

Example 11

40 g (0.014 mole) of fluoroanhydride of perfluoro-n-polyoxapropylene-carboxylic acid $[CF_3O(CF_2CF_2CF_2O)_{15}CF_2CF_2COF]$, 3.5 g (0.046 mole) of methoxyethyleneamine ($CH_3OC_2H_4NH_2$), 50 g of Freon-113, and 3.5 g (0.06 mole) KF are mixed together at 0° C. The resultant mixture is boiled with a refluxer under stirring for 40 min, whereupon the reaction mass is washed three times in succession with 70 ml of distilled water. The organic layer is separated, purified in a cationic column and in an anionic column, then dried with $MgSO_4$ and filtered, while Freon-113 is distilled off. The stillage residue is extracted three times with 50 ml of isopropyl alcohol. The extract is filtered and the alcohol is distilled off. The resultant methoxyethyleneamide of perfluoro-n-polyoxapropylene-carboxylic acid is vacuum-dried at 1 mm Hg and 50° C. for two hours.

The yield is 22.5 g (55%), the congelation point, –58° C., $F'$=0.0007 wt. %.

IR-spectrum ($CaF_2$), ν, $cm^{-1}$:

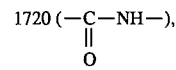

2970 (—$CH_3$).

NMR-spectrum of $^{19}F$ in $CCl_3F$, δ, p.p.m.: 56.0 $CF_3O$—, 81.9 —$OCF_2$—, 130.6 —$CF_2$—, 83.2 —$CF_2O$—, 89.84 —$OCF_2$—, 120.5

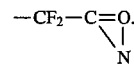

Found, %: C, 22.4; H, 0.31; F, 66.1; N, 0.5. $C_{52}H_8F_{97}O_{18}N$.

Calculated, %: C, 22.4; H, 0.29; F, 66.3 N, 0.5.

Molecular weight of the product is 2760.

Example 12

45 g (0.027 mole) of fluoroanhydride of perfluoropolyoxapropylene-carboxylic acid $[C_2F_5)(CF_2CF_2O)_{12}CF_2COF]$, 2.9 g (0.033 mole) of ethoxyethyleneamine ($C_2H_5OC_2H_4$—$NH_2$), 50 g of Freon-113, and 6 g (0.06 mole) $KHCO_3$ are mixed together at 0° C. The mixture is boiled with a refluxer under stirring for 40 min, whereupon the reaction mass is washed three times in succession with 50 ml of distilled water. The organic layer is separated, purified in a cationic column and in an anionic column, then dried with $Na_2SO_4$ and filtered, while Freon-113 is distilled off. The stillage residue is extracted three times with 40 ml of isopropyl alcohol. The extract is filtered and the alcohol is distilled off. The resultant ethoxyethyleneamide of perfluoropolyoxaethylene-carboxylic acid is vacuum-dried at 1 mm Hg and 50° C. for two hours.

The yield is 37.5 g (80%), the congelation point, –59° C., $F'$=0.0008 wt. %.

IR-spectrum ($CaF_2$), ν, $cm^{-1}$:

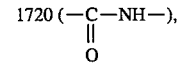

2980 ($CH_3$).

NMR-spectrum of $^{19}F$ in $CCl_3F$, δ, p.p.m.: 88.7 $CF_3$—, 89.5—$CF_2O$—, 91.0 —$COF_2$—,

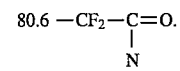

Found, %: C, 22.6; H, 0.7; F, 61.4; N, 0.8. $C_{32}H_{10}F_{55}O_{15}N$.

Calculated, %: C, 22.7; H, 0.6; F, 61.7 N, 0.8.

Molecular weight of the product is 1690.

Example 13

50 g (0.018 mole) of fluoroanhydride of perfluoropoly-oxapropylene-carboxylic acid

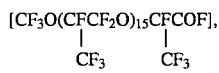
[CF$_3$O(CFCF$_2$O)$_{15}$CFCOF],
    |                    |
   CF$_3$                CF$_3$ 2.4 g (0.023 mole) of prophydroxyethyleneamine, 60 g of Freon-113, and 4.2 g (0,05 mole) NaHCO$_3$ are mixed together at +0° C. The mixture is boiled with a refluxer under constant stirring for 40 min, whereupon the reaction mass is washed three times in succession with 50 ml of distilled water. The organic layer is separated and purified first in a cationic column, then in an anionic column, dried with Na$_2$SO$_4$, and passed through a filter, while Freon-13 is distilled off. The stillage residue is extracted three times in succession with 50 ml of isopropyl alcohol, the extract is filtered, and the alcohol is distilled off. The resultant prophydroxyethyleneamide of perfluoropolyoxapropylene-carboxylic acid is vacuum-dried at 1 mm Hg and 65° C. for two hours. The yield is 42 g (81%), the congelation point, −53° C., F′=0.0009 wt. %.

IR-spectrum (CaF$_2$), ν, cm$^{-1}$:

1725 (—C—NH—),
      ‖
      O 3000 (—CH$_3$).

NMR-spectrum of $^{19}$F in CCl$_3$F, δ, p.p.m.: 56.0 CF$_3$—, 81.0 —CF$_3$, 82.5 —COF$_2$,

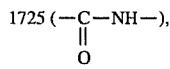
140.8 —OCF—   130.6 OCF—C=O.

Found, %: C, 23.0; H, 0.5; F, 65.2; N, 0.5.
C$_{54}$H$_{12}$F$_{97}$O$_{18}$N.
Calculated, %: C, 23.1; H, 0.4; F, 65.7; N, 0.5.
The molecular weight of the product equals 2800.

Example 14

60 g (0.022 mole) of perfluoropolyoxaethylenesulfo-fluoride [C$_2$F$_5$)(CF$_2$CF$_2$O)$_{20}$CF$_2$CF$_2$SO$_2$F], 4.5 g (0.033 mole) of tetrahydroxyethylene-ethanolamine [H(OCH$_2$CH$_2$)$_5$—NH$_2$], 80 g of Freon-113, and 5 g (0.06 mole) NaHCO$_3$ are mixed together at +5° C. The mixture is boiled with a refluxer under stirring for 50 min, whereupon the reaction mass is washed three times in succession with 60 ml of distilled water. The organic layer is separated, purified in a cationic column and in an anionic column, then dried with MgSO$_4$ and filtered, while Freon-113 is distilled off. The stillage residue is extracted three times with 50 ml of ethyl alcohol. The extract is filtered and the alcohol is distilled off. The resultant tetrahydroxyethylene-ethanolamide of perfluoropolyoxaethylene-sulfo acid is vacuum-dried at 1 mm Hg and 70° C. for 1.5 hours. The yield is 38.9 g (60%), the congelation point, −42° C., F′=0.0008 wt. %.

IR-spectrum (CaF$_2$), ν, cm$^{-1}$: 1420 (—SO$_2$—NH—), 3310 (—OH).

NMR-spectrum of $^{19}$F in CCl$_3$F, δ, p.p.m.: 88.5 CF$_3$—, 89.1 —CF$_2$O—, 91.0 —OCF$_2$—,

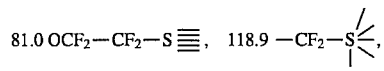
81.0 OCF$_2$—CF$_2$—S≡,   118.9 —CF$_2$—S⧸,

Found, %: C, 23.0; H, 0.8; F, 58.8; N, 0.48; S, 1.1.
C$_{54}$H$_{22}$F$_{89}$O$_{28}$NS.
Calculated, %: C, 22.7; H, 0.76; F, 59.2 N, 0.48; S, 1.1.
Molecular weight of the product is 2850.

Example 15

70 g (0.024 mole) of fluoroanhydride of perfluoropoly-oxapropylene-carboxylic acid

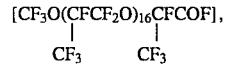
[CF$_3$O(CFCF$_2$O)$_{16}$CFCOF],
    |                    |
   CF$_3$                CF$_3$ 4.3 g (0.029 mole) of triethanolamine, 100 g of Freon-113, and 5 g (0.06 mole) NaHCO$_3$ are mixed together at +5° C. The resultant mixture is boiled with a refluxer under stirring for 60 min, whereupon the reaction mass is washed three times in succession with 60 ml of distilled water. The organic layer is separated, purified in a cationic column and in an anionic column, then dried with MgSO$_4$ and filtered, while Freon-113 is distilled off. The stillage residue is extracted three times with 60 ml of isopropyl alcohol. The extract is filtered and the alcohol is distilled off. The resultant monoester, that is, hydroxyethylene-ethanolamine of perfluoropolyoxaethylene-carboxylic acid

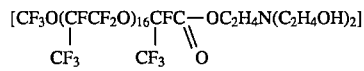
[CF$_3$O(CFCF$_2$O)$_{16}$CFC—OC$_2$H$_4$N(C$_2$H$_4$OH)$_2$]
    |              |    ‖
   CF$_3$         CF$_3$  O is vacuum-dried at 1 mm Hg and 50° C. for 2.5 hours.
The yield is 65.8 g (90%), the congelation point, −46° C., F′=0.008 wt. %.

IR-spectrum (CaF$_2$), ν, cm$^{-1}$:

1780 (—C=O),
      |
      O 3420 (—OH).

NMR-spectrum of $^{19}$F in CCl$_3$F, δ, p.p.m.: 56.1 CF$_3$O—,

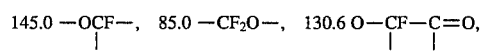
145.0 —OCF—,   85.0 —CF$_2$O—,   130.6 O—CF—C=O, 81.0 CF$_3$.
Found, %: C, 23.2; H, 0.52; F, 64.4; N, 0.5.
C$_{58}$H$_{14}$F$_{103}$O$_{21}$N.
Calculated, %: C, 23.1; H, 0.5; F, 64.8 N, 0.5.
Molecular weight of the product is 3010.

Example 16

60 g (0.029 mole) of fluoroanhydride of perfluoropoly-oxaethylene-carboxylic acid [CF$_3$O(CF$_2$CF$_2$O)$_{16}$CF$_2$COF], 9.5 g (0.041 mole) of tributanolamine, 100 g of Freon-113, and 8 g (0.0 mole) KHCO$_3$ are mixed together at +5° C. The resultant mixture is boiled with a refluxer under stirring for 80 min, whereupon the reaction mass is washed three times in succession with 70 ml of distilled water. The organic layer is separated, purified in a cationic column and in an anionic column, then dried with $MgSO_4$ and filtered, while Freon-113 is distilled off. The stillage residue is extracted three times with 50 ml of isopropyl alcohol. The extract is filtered and the alcohol is distilled off. The resultant monoester, i.e. hydroxybutylenebutanolamine of perfluoropolyoxaethylene-carboxylic acid $[CF_3O(CF_2CF_2O)_{16}CF_2COOC_4H_8N(C_4H_8OH)_2]$ is vacuum-dried at 1 mm Hg and 50° C. for 2.5 hours.

The yield is 42.4 g (64%), the congelation point, −36° C., $F^I$=0.001 wt. %.

IR-spectrum ($CaF_2$), ν, cm$^{-1}$:

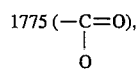

1775 (—C=O), 3450 (—OH).

NMR-spectrum of $^{19}F$ in $CCl_3F$, δ, p.p.m.: 56.0 $CF_3O$, 91.0 —$OCF_2$—,

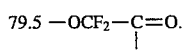

79.5 —$OCF_2$—C=O.

Found, %: C, 25.1; F, 57.9; H, 1.17; N, 0.6. $C_{47}H_{26}F_{69}O_{21}N$.
Calculated, %: C, 25.0; F, 58.2; H, 1.15; N, 0.62.
Molecular weight of the product is 2250.

Example 17

50 g (0.017 mole) of fluoroanhydride of perfluoropolyoxapropylene-carboxylic acid

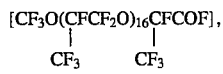

$[CF_3O(CFCF_2O)_{16}CFCOF]$,
    |              |
    $CF_3$        $CF_3$ 6.9 g (0.068 mole) of hexanol, 60 g of Freon-113, and 5.7 g (0.068 mole) $AlF_3$ are mixed together at 0° C. The resultant mixture is boiled with a refluxer under stirring for two hours, whereupon 3 ml (0.17 mole) $H_2O$ is added to the reaction mass and the latter is stirred for another 20 min, whereupon the reaction mass is filtered and purified in a cationic column and in an anionic column. Freon-113 is distilled off from the filtrate, and the residue is extracted three times with 50 ml of sulfuric ether. The traces of sulfuric ether are removed under vacuum at 20 mm Hg and 20° C. for 20 min. The residue is extracted four times with 40 ml of isopropyl alcohol. The extract is dried with $Na_2SO_4$, filtered, and the alcohol is distilled off. The resultant hexyl ester of perfluoropolyoxapropylene-carboxylic acid is vacuum-dried at 1 mm Hg and 50° C. for two hours.

The yield is 36.0 g (70%), the congelation point, −30° C., $F^I$=0.001 wt. %.

IR-spectrum ($CaF_2$), ν, cm$^{-1}$:

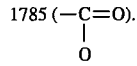

1785 (—C=O).

NMR-spectrum of $^{19}F$ in $CCl_3F$, δ, p.p.m.: 56.0 $CF_3O$,

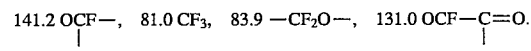

141.2 OCF—,  81.0 $CF_3$,  83.9 —$CF_2O$—,  131.0 OCF—C=O.

Found, %: C, 23.3; H, 0.4; F, 65.5. $C_{58}H_{13}F_{103}O_{19}$.
Calculated, %: C, 23.4; H, 0.4; F, 65.9.
Molecular weight of the product is 2970.

Example 18

40 g (0.014 mole) of fluoroanhydride of perfluorooxaethylene-carboxylic acid $[CF_3O(CF_2CF_2O)_{16}CF_2COF]$, 7.3 g (0,056 mole) of octanol, 50 g of Freon-113, and 4.7 g (0.056 mole) $AlF_3$ are mixed together at 0° C. The resultant mixture is boiled with a refluxer under stirring for three hours, whereupon 2.5 g (0.14 mole) $H_2O$ is added thereto. The reaction mass is stirred for another 30 min and filtered. The filtrate is purified in a cationic column and in an anionic column. Freon-113 is distilled off from the filtrate, and the residue is washed three times with 40 ml of sulfuric ether. The extract is dried with $MgSO_4$, then the solution is filtered and the alcohol is distilled off. The resultant octyl ester of perfluoropolyoxaethylene-carboxylic acid is vacuum-dried at 1 mm Hg and 50° C. for 2.5 hours. The yield is 24.9 g (60%), the congelation point, +28° C., $F^I$=0.006 wt. %.

IR-spectrum ($CaF_2$), ν, cm$^{-1}$:

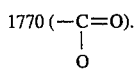

1770 (—C=O).

NMR-spectrum of $^{19}F$ in $CCl_3F$, δ, p.p.m.: 55.8 $CF_3O$—, 91.0 $OCF_2$—, 80.3 $OCF_2$—C=O.

Found, %: C, 23.8; H, 0.8; F, 61.1. $C_{43}F_{69}O_{19}H_{17}$.
Calculated, %: C, 24.0; H, 0.8; F, 61.0.
Molecular weight of the product is 3000.

Example 19

55 g (0.02 mole) of fluoroanhydride of perfluoro-n-polyoxapropylene-carboxylic acid $[CF_3O(CF_2CF_2CF_2O)_{15}CF_2CF_2COF]$, 15.8 g (0.10 mole) of decanol, 80 g of Freon-113, and 8.4 g (0.1 mole) $AlF_3$. The resultant mixture is boiled with a refluxer under stirring for three hours, whereupon 18 g (0.14 mole) $H_2O$ is added thereto. The reaction mass is stirred for another 30 min and filtered. The filtrate is purified in a cationic column and in an anionic column. Freon-113 is distilled off from the filtrate and the residue is washed four times with 50 ml of petroleum ether. The washed product is vacuumized for the ether traces to eliminate, and is extracted four times with 50 ml of n-propanol. Then the extract is dried with $MgSO_4$ and filtered, and the alcohol is distilled off. The resultant decyl ester of perfluoro-n-polyoxaethylene-carboxylic acid is vacuum-dried at 1 mm Hg and 60° C. for 2.5 hours.

The yield is 26.1 g (45%), the congelation point, +36° C., $F^I$=0.004 wt. %.

IR-spectrum ($CaF_2$), ν, cm$^{-1}$:

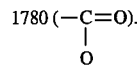

1780 (—C=O).

NMR-spectrum of $^{19}F$ in $CCl_3F$, δ, p.p.m.: 56.0 $CF_3O$—, 83.0 —$OCF_2$—, 130.4 —$CF_2$—, 83.0 —$CF_2$—O, 82.3 $OCF_3$—, 119.3

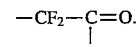

—$CF_2$—C=O.

Found, %: C, 24.5; H, 0.75; F, 64.3. $C_{59}H_{21}F_{97}O_{18}$.
Calculated, %: C, 24.7; H, 0.7; F, 64.4.
Molecular weight of the product is 2860.

Example 20

30 g (0.02 mole) of fluoroanhydride of perfluoropolyoxapropylene-carboxylic acid $$[CF_3O(CFCF_2O)_8CFCOF],$$
$$\quad\quad\quad\quad\quad |\quad\quad\quad |$$
$$\quad\quad\quad\quad\quad CF_3\quad\quad CF_3$$

2.83 g (0.027 mole) of diethanolamine, 1.1 g (0.03 mole) $NH_4F$, and 55 g of perfluoro-à-propylfuranidine are mixed together at $-25°$ C. The resultant mixture is heated with a refluxer under stirring for 40 min, whereupon the reaction mass is washed three times in succession with 50 ml of distilled water. Once dehydrated the reaction mass is purified first in a cationic column, then in an anionic column, dried with fused $Na_2SO_4$ and filtered. Next perfluoro-à-propylfuranidine is distilled off from the filtrate and the residue is dried under vacuum at a residual pressure of 1 mm Hg and a temperature of 40° C. for 60 min. The stillage residue is diethanolamide of perfluoropolyoxapropylene-carboxylic acid.

The yield is 29.7 g (93%), the congelation point, $-65°$ C. , $F'=0.0021$ wt. %.

IR-spectrum ($CaF_2$), $v$, $cm^{-1}$:

$$1725\ (-\underset{\underset{O}{\|}}{C}-N),$$

330 (—OH).

NMR-spectrum of $^{19}F$ in $CCl_3F$, δ, p.p.m.: 55.5 $CF_3O$—, 82.6 —$OCF_2O$—, $$143.8\ -OCF-,\quad 80.8\ -CF_3,\quad 130.2\ -\underset{\underset{O}{\|}}{CF}-\underset{}{C}-$$

Found, %: C, 23.1; H, 0.59; F, 62.9; N, 0.86. $C_{32}H_{10}F_{55}O_{12}N$.

Calculated, %: C, 23.3; H, 0.6; F, 63.5 N, 0.85.

Molecular weight of the product is 1640.

Example 21

25 g (0.018 mole) of perfluoropolyoxaethylenesulfo-fluoride $[C_2F_5)(CF_2CF_2O)_{10}CF_2CF_2SO_2F]$, 8.1 g (0.077 mole) of diethanolamine, 1.45 g (0.025 mole ) KF, and 50 ml of 1,4-dihydrooctafluorobutane $[CF_2H-CF_2CF_2-CF_2H]$. The resultant mixture is heated to 40° C. with a refluxer under stirring and held at that temperature for five hours, whereupon the reaction mass is washed three times in succession with 50 ml of distilled water and purified first in cationic column and then in an anionic column. Then the reaction mass is dried with $Na_2SO_4$ and filtered, the solvent $CF_2HC_2F_4CF_2H$ is distilled off from the filtrate and the residue is dried at 1 mm Hg and 50° C. for two hours.

The yield is 20.1 g (77.8%) the congelation point, $-44°$ C., $F'=0.001$ wt. %.

IR-spectrum ($CaF_2$), $v$, $cm^{-1}$: 1425 (—$CF_2$—$SO_2$—N=), 3330 (—OH).

NMR-spectrum of $^{19}F$ in $CCl_3F$, δ, p.p.m.: 55.3 $CF_3O$—, 91.2 —$CF_2O$, 86.0 $CF_2$—$CF_2$—S, $$1119.3\ -CF_2-\underset{\underset{\|}{\|}}{S}-$$

Found, %: C, 21.7; H, 0.70; F, 58.9; N, 0.91, S 1.98. $C_{28}H_{10}F_{49}O_{15}NS$.

Calculated, %: C, 21.5; H, 0.64; F, 59.5 N, 0.90; S, 2.00.

Molecular weight of the product is 1560.

The compounds produced according to Examples 1–21 are soluble and emulsifiable in lubricating oils and hence require no emulsifier.

We claim:

1. Amides and esters of perfluoropolyoxaalkylene-sulfo- or perfluoropolyoxaalkylene-carboxylic acids of the general following formula:

$R_F R_F' ZQ$, where $R_F = CF_3O$—, $C_2F_5O$—, $C_3F_7O$—, $C_8F_{17}O$—, $R_F' =$ $$-(CFCF_2O)_nCF-,$$
$$\quad\quad |\quad\quad\quad\quad |$$
$$\quad\quad CF_3\quad\quad\ CF_3$$

—$(CF_2CF_2O$—$)_nCF_2$—, —$(CF_2CF_2CF_2O)_nCF_2CF_2$—, where n=8–55;

Z=—CO—, —$SO_2$—,

Q=—$N(C_mH_{2m}OH)_2$, where m=2, 3, 4, 6, 8, 10

—$N[(C_2H_4O)_4C_3H_6OH]_2$,

—NH—$C_2H_4OR_η$, where $R_η$=$CH_3$—, $C_2H_5$—, $C_3H_7$—,

—$NH(C_2H_4O)_5H$,

—$OC_lH_{2l}N(C_lH_{2l}OH)_2$, where η=1, 2, 4

$C_kH_{2k+1}O$—, where k=6, 8, 10.

2. A process for producing amides and esters of perfluoropolyoxaalkylene-sulfo- or perfluoropolyoxaalkylene-carboxylic acids of the general following formula:

$R_F R_F' ZQ$, where $R_F = CF_3O$—, $C_2F_5O$—, $C_3F_7O$—, $C_8F_{17}O$—, $R_F' =$ $$-(CFCF_2O)_nCF-,$$
$$\quad\quad |\quad\quad\quad\quad |$$
$$\quad\quad CF_3\quad\quad\ CF_3$$

—$(CF_2CF_2O$—$)_nCF_2$—,

—$(CF_2CF_2CF_2O)_nCF_2CF_2$—, where n=8–55;

Z=—CO—, —$SO_2$—,

Q=—$N(C_mH_{2m}OH)_2$, where m=2, 3, 4, 6, 8, 10

—$N[(C_2H_4O)_4C_3H_6OH]_2$,

—NH—$C_2H_4OR_η$, where $R_η$=$CH_3$—, $C_2H_5$—, $C_3H_7$—,

—$NH(C_2H_4O)_5H$,

—$OC_lH_{2l}N(C_lH_{2l}OH)_2$, where η=1, 2, 4

$C_kH_{2k+1}O$—, where k=6, 8, 10, wherein the fluoroanhydride of perfluoropolyoxaalkylene-sulfo- or perfluoropolyoxaalkylene-carboxylic acid has the following general formula:

$R_F R_F' ZQ$—, where $R_F = CF_3O$—, $C_2F_5O$—, $C_3F_7O$—, $C_8F_{17}O$—, $R_F' =$ $$-(CFCF_2O)_nCF-,$$
$$\quad\quad |\quad\quad\quad\quad |$$
$$\quad\quad CF_3\quad\quad\ CF_3$$

$(CF_2CF_2O$—$)_nCF_2$—, —$(CF_2CF_2CF_2O)_nCF_2CF_2$—, where n=8–55;

Z=—CO—, —$SO_2$—, is mixed at a temperature of from −25° to +8° C. with a secondary, or tertiary amine or alkanolamine of a general formula:

$H_{3-x}N(R)_x$, where x=1, 2, 3

$R=(C_nH_{2n}OH)_x$, where n=2, 3, 4, 6, 8, 10

—$[(C_2H_4O)_4C_3H_6OH]_x$, with x=2,

—$(C_2H_4OCH_3)_x$,

—$(C_2H_4OC_2H_5)_x$,

—$(C_2H_4OC_3H_7)_x$, with x=1,

—$[(C_2H_4O)_5H]_x$, and

—$(C_nH_{2n}OH)_x$, where n=2, 4 with x=3, or with a higher fatty alcohol of a general formula:

$C_nH_{2n+1}OH$, where n=6, 8, 10, and a compound selected from the group consisting of a fluoride of an alkali- and an alkaline-earth metal, ammonium fluoride, aluminium fluoride, carbonates of metals and bicarbonates of metals, with a molar ratio between said components of 1.0:1.2 to 4.0:1.5–3.0, respectively, followed by heating the reaction mixture to 40°–60° C., holding said mixture at that temperature for 0.6 to 3.0 hours and isolating the end product from the resultant reaction mass.

3. A process according to claim 2, wherein the reactants are mixed together in the presence of a polyfluorocarbon solvent having a boiling point of from 40° to 60° C.

4. A process according to claim 2, wherein polyfluorocarbon solvent is trifluorotrichloroethane or perfluorotriethylamine.

* * * * *